United States Patent
Muppa et al.

(10) Patent No.: US 9,174,955 B2
(45) Date of Patent: *Nov. 3, 2015

(54) MANUFACTURE OF AN EPOXYETHYL CARBOXYLATE OR GLYCIDYL CARBOXYLATE

(75) Inventors: Prasad Muppa, Vondelingenplaat (NL); Ron Postma, Vondelingenplaat (NL); Caspar Schoolderman, Vondelingenplaat (NL); Sandra Rens, Vondelingenplaat (NL); Kostas Stoitsas, Vondelingenplaat (NL)

(73) Assignee: HEXION INC., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/574,693

(22) PCT Filed: Jan. 26, 2011

(86) PCT No.: PCT/EP2011/000322
§ 371 (c)(1),
(2), (4) Date: Sep. 7, 2012

(87) PCT Pub. No.: WO2011/095294
PCT Pub. Date: Aug. 11, 2011

(65) Prior Publication Data
US 2013/0006001 A1   Jan. 3, 2013

(30) Foreign Application Priority Data

Feb. 2, 2010   (EP) ..................................... 10001034

(51) Int. Cl.
*C07D 303/12* (2006.01)
*C07D 301/12* (2006.01)
*C07D 303/48* (2006.01)

(52) U.S. Cl.
CPC ............ *C07D 301/12* (2013.01); *C07D 303/48* (2013.01)

(58) Field of Classification Search
CPC ........................... C07D 303/16; C07D 303/12
USPC .......................................................... 549/561
See application file for complete search history.

(56) References Cited

U.S. PATENT DOCUMENTS

| | | | |
|---|---|---|---|
| 4,021,454 A | 5/1977 | Wulff et al. | |
| 4,038,291 A | 7/1977 | Gipson | |
| 4,127,594 A | 11/1978 | Anderson et al. | |
| 4,973,718 A | 11/1990 | Buchler | |
| 5,153,161 A | 10/1992 | Kershner et al. | |
| 5,155,274 A | 10/1992 | Hermann et al. | |
| 5,274,147 A | 12/1993 | Kershner et al. | |
| 5,329,024 A | 7/1994 | Jureller et al. | |
| 5,429,769 A | 7/1995 | Nicholson et al. | |
| 5,516,738 A | 5/1996 | Jureller et al. | |
| 5,532,389 A | 7/1996 | Trent et al. | |
| 5,833,755 A | 11/1998 | Schlon et al. | |
| 6,087,513 A | 7/2000 | Liao et al. | |
| 6,500,968 B2 | 12/2002 | Zhou et al. | |
| 6,673,950 B1 | 1/2004 | Teles et al. | |
| 8,729,282 B2 * | 5/2014 | Postma et al. | ................. 549/531 |
| 2001/0025695 A1 | 10/2001 | Patt et al. | |
| 2002/0010120 A1 | 1/2002 | Hage et al. | |
| 2006/0041150 A1 | 2/2006 | Catinat et al. | |
| 2010/0029848 A1 | 2/2010 | Forlin et al. | |
| 2012/0330041 A1 | 12/2012 | Muppa et al. | |

FOREIGN PATENT DOCUMENTS

| | | |
|---|---|---|
| CN | 1900071 | 1/2007 |
| DE | 19923121 | 11/2000 |
| EP | 0458397 | 5/1991 |
| EP | 0458398 | 5/1991 |
| EP | 0618202 A1 | 10/1994 |
| EP | 1403219 | 3/2004 |
| EP | 1883730 | 2/2008 |
| EP | 2149569 | 2/2010 |
| EP | 2149569 A1 | 2/2010 |
| EP | 2149570 | 2/2010 |
| EP | 2402087 | 1/2012 |
| JP | 2002145872 | 5/2002 |
| TW | 305831 | 6/1995 |
| TW | 200823183 | 6/2008 |
| WO | WO 2007/046960 | 4/2007 |

OTHER PUBLICATIONS

Vos et al. Tetrahedron Letters, 39, 1998, 3221-3224.*
Murphy et al Organic Letters, 2004, 6(18), 3119-3122.*
De Boer et al. Inorganic Chemistry, 46(16), 6353-6372, 2007.*
De Vos et al.Tetrahedron Letters, 1998, 39, 3221-3224.*
D.E. De Vos et al., Tetrahedron Letters, vol. 39, No. 20 (1998) 3221-3224.
N.O. Brace et al., Journal of Organic Chemistry vol. 26, (1961) 5176-5180.
J.W. De Boer, "cis-Dihydroxylation and Epoxidation of Alkenes by Manganese Catalysts Selectivity, Reactivity and Mechanism", Feb. 22, 2008, Dissertation, University of Groningen, PrintPartners Ipskamp BV, Enschede, the Netherlands.
(Continued)

Primary Examiner — Nizal Chandrakumar

(57) ABSTRACT

The invention relates to a process for the manufacture of an epoxyethyl carboxylate or glycidyl carboxylate, including reacting a vinyl carboxylate or an allyl carboxylate using an oxidant and a water-soluble manganese complex in an aqueous reaction medium, and the water-soluble manganese complex comprises an oxidation catalyst, characterized in that the water-soluble manganese complex is a mononuclear species of the general formula (I) [LMnX$_3$]Y (I), or a binuclear species of the general formula (II): [LMn(μ-X)$_3$MnL]Y$_n$ (II), wherein Mn is a manganese; L is a ligand and each L is independently a polydentate ligand, each X is independently a coordinating species and each μ-X is independently a bridging coordinating species, Y is a non-coordinating counter ion, and wherein the epoxidation is carried out at a pH in the range of from 1.0 to 7.0.

16 Claims, No Drawings

(56) References Cited

OTHER PUBLICATIONS

J.W. De Boer, "Mechanism of Cis-Dehydroxylation and Epoxidation of Alkenes by Highly H2O2 Efficient Dinuclear Managanese Catalysts." with Online Supporting Information, Inorganic Chemistry (2007), vol. 46, No. 16, pp. 6353-6372, American Chemical Society.

A. Grenz et al., "Synthesis and application of novel catalytically active polymers containing 1,4,7-triazacyclononanes", Chem. Commun. (2001) No. 18, 1726-1727 (Cambridge, England).

A. Murphy et al., "Ligand and pH Influence on Manganese-Mediated Peracetic Acid Epoxidation of Terminal Olefins", Organic Letters, (2004) vol. 6 No. 18, 3119-3122.

Z. Xi Et al., "An Enviromentally Benign Route for Epochlorohydrin From Allyl Chloride Epoxidation Catalyzed by Heteropolyphophatotungstate", Research on Chemical Intermediates (2007) vol. 33, No. 6, 523-534, VSP.

\* cited by examiner

MANUFACTURE OF AN EPOXYETHYL CARBOXYLATE OR GLYCIDYL CARBOXYLATE

RELATED APPLICATION DATA

This application claims the benefit of PCT Application PCT/EP2011/000322 with an International Filing Date of Jan. 26, 2011, published as WO 2011/095294, which PCT Application PCT/EP2011/000322 further claims priority to European Patent Application No. EP10001034.7 filed Feb. 2, 2010, the entire contents of both are hereby incorporated by reference.

FIELD OF INVENTION

The invention relates to a process for the manufacture of an epoxyethyl carboxylate or glycidyl carboxylate by reacting a vinyl carboxylate or an allyl carboxylate with an oxidant in the presence of a manganese complex.

BACKGROUND OF INVENTION

Glycidyl esters are an important starting material in the chemical industry. The glycidyl esters are typically prepared by reaction of epichlorohydrin with a carboxylic acid in the presence of catalyst and subsequent dehydrochlorination of the resulting mixture of chlorohydrin esters followed by their separation. In particular the glycidyl esters of branched carboxylic acids and epoxy specialties are of commercial importance, which find use in the production of high-grade alkyd resins, polyester resins, acrylic resins, and a variety of other resins, and also as reactive diluent. Of particular interest are the glycidyl esters commercialized under the CARDURA™ trademark, which have been used for decades as a building block for automotive OEM, Refinish and CED coatings. The Glycidyl Ester of Versatic™ acid exhibits UV stability, acid etch resistance and a unique ability to create high solids low viscosity polymers with good substrate wetting.

Of similar interest is the 1,2-epoxyethyl carboxylate, for instance the product of the epoxidation of vinyl pivalate and in particular the product of the epoxidation of a vinyl ester of a branched carboxylic acid. Such esters are commercially available under the VEOVA™ trademark.

Epoxidation of vinyl esters or allyl esters is uncommon. According to the literature it is possible to epoxidize vinyl acetate by using a Ti-MWW/$H_2O_2$ catalytic system ("Epoxidation of Various Functionalized Olefins by a Ti-MWW/$H_2O_2$ Catalytic System", by LI Ningnin et al in Chin J Catal, 2008, 29(2): 102-104). From this reference it is known that the epoxidation of a C=C bond is more difficult when the C=C bond is connected to groups having a high electron drawing group. The epoxidation of vinyl esters is even more difficult than the epoxidation of allyl esters. This is because the C=C bond in the vinyl group is conjugated with the C=O bond or adjacent to the C—O bond, which makes it electronically more deficient than the C=O bond in the allyl group. The conversion and product selectivity of, for example, allyl acetate epoxidation were higher than that of vinyl acetate epoxidation.

In "Synthesis of some epoxy vinyl monomers by epoxidation with peracetic acid" by F. C. Frostick et al, JACS, 81 (1958) 3350, the epoxidation of vinylpent-4-enoate is described, resulting in the production of vinyl 4,5-epoxypentanoate. The vinyl group is not epoxidized. In the same report reaction constants are given for reaction esters (vinyl acetate, ethyl acrylate, allyl acetate, allyl ether). As can be concluded from the reaction constants, epoxidation of esters is very slow (in some cases does not happen like vinyl acetate and ethyl acrylate).

In EP0618202 various olefins such as 4-vinylbenzoic acid, styrylacetic acid, trans-3-hexenoic acid, trans-2-hexenoic acid and allyl alcohol are epoxidized by contact with a source of oxygen and a Mn complex, such as a binuclear manganese complex, in which the Mn is co-ordinated to an N-containing ligand such that there is a ratio of Mn to co-ordinated N atoms of 1:3. Suitable olefins include compounds with from 2 to 50 carbon atoms, such as those having from 3 to 20 carbon atoms. They may be selected from mono- or multi-substituted and unsubstituted, branched or unbranched alkenes and arylalkenes. Substitution of the alkenes may be in the form of hetero atom functional groups including those of halo, cyano, carboxylate, sulphate, phosphate, amino, hydroxyl, nitro, alkoxy, acyloxy and combinations thereof. When the epoxidation process is conducted in an aqueous media, best results are obtained on olefins with water-soluble groups such as those with carboxylate and hydroxyl units, e.g. vinylbenzoic acid, styrylacetic acid and hexenoic acid. This reference does not disclose the epoxidation of vinyl carboxylates or allyl carboxylates.

The inventors set out to find an alternative route to glycidyl esters of carboxylic acids that does not rely on epichlorohydrin. Such an alternative route has been found. Moreover, this new route also opens the possibility of preparing epoxyethyl esters of carboxylic acids which will find use in the same applications where the glycidyl esters are used.

The present invention provides an attractive route to such products.

DISCLOSURE OF THE INVENTION

Accordingly, the invention provides a process for the manufacture of an epoxyethyl carboxylate or glycidyl carboxylate, comprising:

reacting a vinyl carboxylate or an allyl carboxylate using an oxidant and a water-soluble manganese complex in an aqueous reaction medium, wherein the water-soluble manganese complex comprises an oxidation catalyst, characterized in that the water-soluble manganese complex is a mononuclear species of the general formula (I):

$$[LMnX_3]Y \qquad\qquad (I),$$

or a binuclear species of the general formula (II):

$$[LMn(\mu\text{-}X)_3MnL]Y_n \qquad\qquad (II),$$

wherein Mn is a manganese; L is a ligand and each L is independently a polydentate ligand, each X is independently a coordinating species and each µ-X is independently a bridging coordinating species, whereas Y is a non-coordinating counter ion, and wherein the epoxidation is carried out at a pH in the range of from 1.0 to 7.0

The epoxidation products of the vinyl esters of highly branched acids are believed to be novel. Accordingly, this invention also relates to epoxyethyl esters of neoacids (wherein R is a tertiary alkyl group) having from 5 to 30 carbon atoms in the acid moiety.

MODE(S) FOR CARRYING OUT THE INVENTION

As used in the current specification, the expressions epoxidation and oxidation refer to the same reaction; the conversion of the carbon-carbon double bond of the vinyl group or the allyl group into an oxirane ring. The invention is hereafter discussed in greater detail.

It is rather surprising that the current process can be used to prepare epoxyethyl carboxylates and glycidyl carboxylates (for example, 1,2-epoxyethyl carboxylate RCOOCH—CH$_2$O; respectively 2,3-epoxypropyl carboxylate, RCOOCH$_2$CH—CH$_2$O) with improved selectivity with having the reaction performed in an aqueous reaction medium. For example, glycidyl carboxylates of allyl esters have an improved selectivity towards epoxide products in comparison other components, such as diols, of from 80% or greater.

In terms of water-soluble manganese complexes that may be used as oxidation catalyst, many suitable complexes are known. Note in this respect that what is described in this patent is actually the catalyst precursor. Indeed, in all open and patent literature typically a catalyst precursor is defined, as the active species during the system may be different and in fact even changing during the reaction that it catalyzes. For convenience sake, and as this is common in the literature, we refer to the complex as if the complex is the catalyst.

In one embodiment, the catalyst comprises a manganese atom or a number of manganese atoms coordinated with a ligand or ligands. The manganese atom(s) may be in a II, III or IV oxidation state and may be activated during the reaction. Of particular interest are binuclear manganese complexes. Suitable manganese complexes therefore include mononuclear species of the general formula (I):

[LMnX$_3$]Y        (I), and binuclear species of the general formula (II):

[LMn(μ-X)$_3$MnL]Y$_n$,        (II), wherein Mn is a manganese; each L is independently a polydentate ligand. The polydentate may be a cyclic or acyclic compound containing 3 nitrogen atoms. Each X is independently a coordinating species and each μ-X is independently a bridging coordinating species, selected from the group consisting of: RO$^-$, Cl$^-$, Br$^-$, I$^-$, F$^-$, NCS$^-$, N$_3^-$, I$_3^-$, NH$_3$, NR$_3$, RCOO$^-$, RSO$_3^-$, RSO$_4^-$, OH$^-$, O$^{2-}$, O$_2^{2-}$, HOO$^-$, H$_2$O, SH$^-$, CN$^-$, OCN$^-$, and S$_4^{2-}$ and combinations thereof, wherein R is a C$_1$-C$_{20}$ radical selected from the group consisting of alkyl, cycloalkyl, aryl, benzyl and combinations thereof. Y is a non-coordinating counter ion. The non-coordinating counter ion Y may provide for the charge neutrality of the complex and the value of n depends upon the charge of the cationic complex and anionic counter ion Y, for example, n may be 1 or 2. Counter ion Y may for instance be an anion selected from the group consisting of RO$^-$, Cl$^-$, Br$^-$, I$^-$, F$^-$, SO$_4^{2-}$, RCOO$^-$, PF$_6^-$, tosylate, triflate (CF$_3$SO$_3^-$) and a combination thereof, with R once again being a C$_1$ to C$_{20}$ radical selected from the group consisting of alkyl, cycloalkyl, aryl, benzyl and combination thereof. The type of anion is not very critical, although some anions are more preferred than others. In one embodiment, an ion of CH$_3$COO$^-$ or PF$_6^-$ may be used as the non-coordinating counter ion.

Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). A preferred ligand is 1,4,7-trimethyl-1,4,7,-triazacyclononane (TmTacn), which is commercially available from for instance Aldrich. In this respect it is important to note that the water-solubility of the manganese catalyst is a function of all the aforementioned catalyst components.

Binuclear manganese complexes are preferred, because of their greater activity and solubility in water. Preferred binuclear manganese complexes are those of the formula [Mn$^{IV}_2$(μ-O)$_3$L$_2$]Y$_n$, (same as formula: [LMn(μ-O)$_3$MnL]Y$_n$), wherein n is 2, and L and Y have the meaning identified above, such as TmTacn as ligand, and CH$_3$COO$^-$ as counter ion.

According to the present invention, the manganese complex may be utilized directly or as adsorbed onto a solvent insoluble support surface. Illustrative but non-limiting examples of such substrates are structured aluminosilicates (e.g. Zeolite A, faujasite and sodalite), amorphous aluminosilicates, silica, alumina, charcoal, microporous polymeric resins (e.g. polystyrene beads formed through high internal phase emulsion technology) and clays (especially layered clays such as hectorite and hydrotalcite). Relative weight ratios of the manganese complex to the support may range anywhere from about 10:1 to about 1:10,000.

The manganese complex may be used in the process in catalytically effective amounts. To achieve the high selectivity and turnover numbers of the current invention, the catalyst and oxidant may be combined for reaction with the vinyl carboxylate or allyl carboxylate at a molar ratio of catalyst to oxidant from 1:100 to 1:10,000,000, such as from 1:500 to 1:100,000, for example, from 1:1000 to 1:50,000. In one embodiment, the catalyst may be used in a molar ratio of catalyst (Mn) to hydrogen peroxide in the range from 1:10 to 1:10,000,000, such as of from 1:20 to 1:100,000, for example, of from 1:50 to 1:50,000. The carboxylate may be used in excess over the oxidant.

An advantage of the current invention, using a water soluble manganese complex is that the catalyst essentially does not migrate to the organic phase.

The molar ratio of a vinyl carboxylate or allyl carboxylate to oxidant affects the reaction and the products of the reaction. For example, if too much oxidant, such as hydrogen peroxide is used, then the selectivity towards the desired epoxide reduces due to the production of undesirable side-products, such as diols, or involves a significant waste of the oxidant. If not enough oxidant is used, then the turnover number is suboptimal. This is therefore significantly different from bleaching conditions described in the prior art, where excessive amounts of an oxidant, such as hydrogen peroxide, are used. The molar ratio of vinyl carboxylate or allyl carboxylate to an oxidant, such as hydrogen peroxide, may be in the range of from greater than 1:2. The molar ratio of vinyl carboxylate or allyl carboxylate to an oxidant, such as hydrogen peroxide, may be in the range from greater than 1:2 to about 12:1, such as from about 1:1 to about 10:1 (or alternatively, from about 1:1.2 to about 2:1, or from 2:1 to 12:1), for example, about 1:1 or 2.3:1. The vinyl carboxylate or allyl carboxylate may be used in excess over the oxidant.

Depending on the reaction conditions, the reaction may be performed in a system having two or more phases (multiphasic), such as an aqueous phase and having at least one organic phase. For example, a two layer system (biphasic) comprising an organic phase and an aqueous phase.

The aqueous reaction medium may be a water phase containing the vinyl carboxylate or allyl carboxylate and/or their respective epoxidation products and less than 10% by volume, preferably only minor amounts, if any, of other organic compounds including co-solvents. Although not preferred, the reaction medium may contain minor amounts of co-solvents, for example, including acetone, methanol, and other water-soluble alcohols. Whilst excluding the presence of the reactants and their epoxidation products, the aqueous reaction medium therefore suitably comprises at least 90% by volume of water (v %), such as 95 v %, for example, 99 v %, and in one embodiment, 99.9 v % of water. The aqueous reaction medium (again, excluding any vinyl carboxylate or allyl carboxylate and/or the corresponding oxides dissolved therein) may be essentially a 100% water phase.

The aqueous reaction medium may contain a buffer system so as to stabilize the pH. For instance, it has been found that the aqueous reaction medium is suitably stabilized in a pH range of 1.0 to 7.0, whereas the preferred pH range is between 2 and 5.0. The suitable or preferred range may be achieved by several known organic acid-salt combinations, with the preferred combination being based on oxalic acid-oxalate salt, or acetate acid-acetate salt or oxalic acid-oxalate salt and acetic acid-acetate salt. When oxalic acid and sodium oxalate are used, the pH ratio may be varied from 2.0 to 6.0. The buffer may be used in a molar ratio to the catalyst of about 60:1, but the amounts may be varied broadly, for example, ranging from 1:1 to 300:1.

The aqueous reaction medium may also contain a phase transfer agent and/or a surfactant. Known phase transfer agents that may be used in the process of the invention include quaternary alkyl ammonium salts. Known surfactants that may be used in the process of the invention include non ionic surfactants such as Triton X100™ available from Union Carbide.

It is believed that the aqueous reaction medium contains at least trace amounts of the starting vinyl carboxylate or allyl carboxylate. Although this is purely a hypothesis, it is believed that the presence of this starting material is beneficial to allow the catalyst to remain active, whereas it is believed that without the presence of the vinyl carboxylate or allyl carboxylate (and/or due to the presence of the epoxidized product and/or oxidant without any starting material), the catalyst has a reduced activity.

The reaction conditions for the catalytic oxidation may be quickly determined by a person skilled in the art. The epoxidation is carried out either under pressure or at atmospheric pressure. The reaction is believed to be exothermic, and cooling of the reaction medium may be required. The reaction may be carried out at temperatures anywhere from 5° C. to 40° C., such as from 5° C. to 30° C.

The carboxylate used in the process of the current invention may be a vinyl ester or allyl ester of a carboxylic acid. This may be a monocarboxylic acid, a dicarboxylic acid or a polycarboxylic acid. The number of vinyl or allyl ester groups may correspond to or be less than the number of acid groups on the carboxylic acid. Thus, the starting material used in the current invention can be a vinyl or allyl ester of a monocarboxylic acid, and diesters of dicarboxylic acids and polyesters of polycarboxylic acids may be used as well. The starting material may be represented by the following formulae:

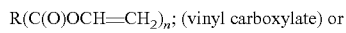

R(C(O)OCH=CH$_2$)$_n$; (vinyl carboxylate) or

R(C(O)OCH$_2$CH=CH$_2$)$_n$,(allyl carboxylate)

wherein R is a mono or polyvalent radical of 1 or more carbon atoms, such as from 2 to 100, for example from 2 to 30 carbon atoms, wherein R optionally contains 1 or more heteroatoms, wherein n corresponds to the number of ester groups, and wherein n is an integer of 1 or greater, such as ranging from 1 to 6. Additionally, R may comprise a secondary alkyl group of from 3 to 100 carbon atoms, such as from 3 to 30 carbon atoms, wherein R optionally contains 1 or more heteroatoms, and/or a tertiary alkyl group of from 4 to 100 carbon atoms, such as from 4 to 30 carbon atoms, wherein R optionally contains 1 or more heteroatoms. The term "neo" refers to highly branched acids. The carboxylic acid can be olefinically unsaturated, such as (meth)acrylic acid. The carboxylic acid may also be aromatic in nature; the aromatic unsaturated bonds are not epoxidized in the current process.

Suitable groups of compounds for use with the process described herein includes mono, bis (di), tris (tri), and poly-allyl esters of aliphatic secondary, aliphatic tertiary, and non-aromatic cyclic compounds. Further examples of suitable groups of compounds include aliphatic functionalized allyl esters of nine or more carbon atoms, aromatic mono or di allyl esters of 15 carbon atoms or more, aromatic functionalized mono, bis, tris, or poly allyl esters of 11 or more carbon atoms, non-aromatic cyclical mono or di allyl esters, tri allyl esters, and combinations thereof.

In one embodiment, suitable group of compounds for use with the process described herein include mono, bis (di), tris (tri), and poly-allyl esters of aliphatic secondary, aliphatic tertiary, and non-aromatic cyclic compounds, aliphatic functionalized allyl esters of nine or more carbon atoms, aromatic functionalized mono, bis tris or poly allyl esters of 11 or more carbon atoms, and combinations thereof.

An example list of suitable allyl esters includes the following esters:

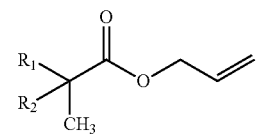

R$_1$ + R$_2$ contain combined 7 carbons
allyl ester of neoacid

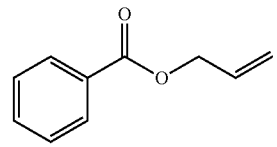

allyl benzoate

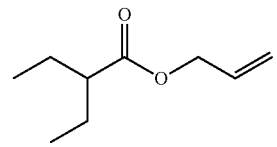

allyl 2-ethylbutanoate

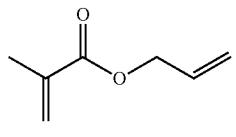

allyl methacrylate

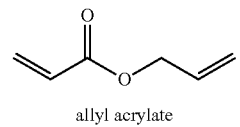

allyl acrylate

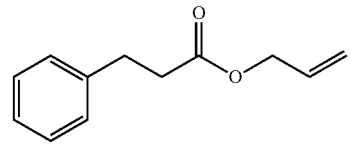

allyl 3-phenylpropanoate

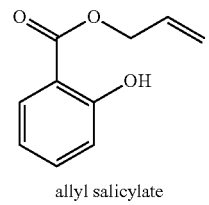

allyl salicylate

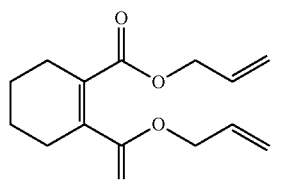

diallyl cyclohex-1-ene-
1,2-dicarboxylate

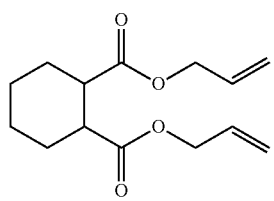

diallyl cyclohexane-
1,2-dicarboxylate

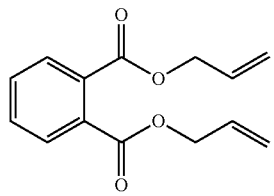

diallyl phthalate

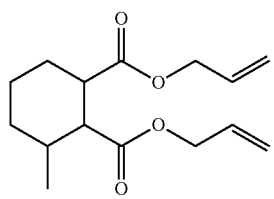

diallyl 3-methylcyclohexane-
1,2-dicarboxylate

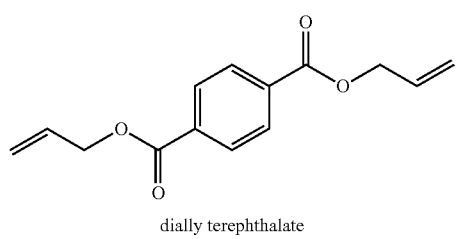

dially terephthalate

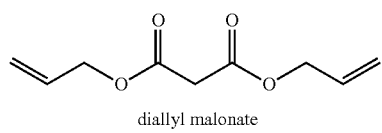

diallyl malonate

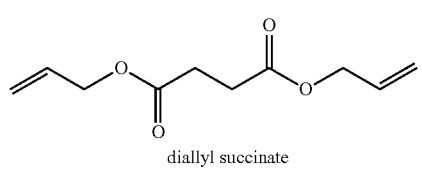

diallyl succinate

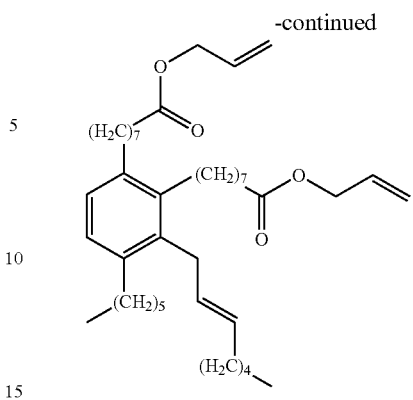

diallyl 8,8'-(4-hexyl-3-(oct-2-en-1-
yl)-1,2-phenylene)dioctanoate

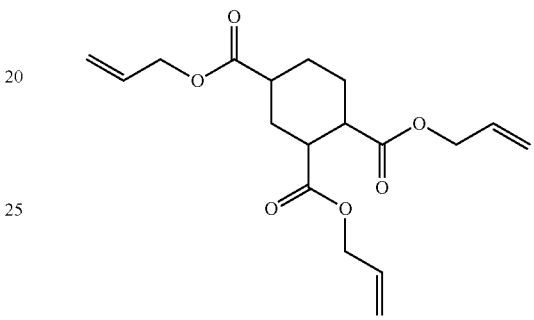

triallyl cyclohexane-1,2,4-tricarboxylate

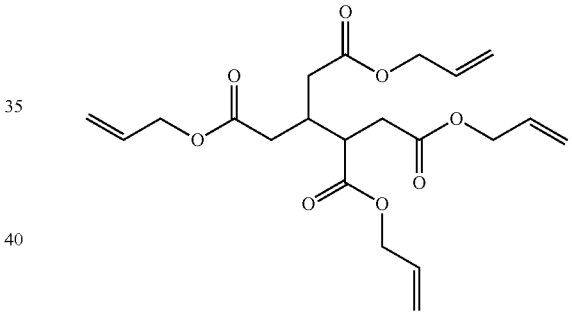

triallyl 3-(2-(allyloxy)-2-oxoethyl)butane-1,2,4-tricarboxylate

The diallyl 8,8'-(4-hexyl-3-(oct-2-en-1-yl)-1,2-phenylene) dioctanoate may also be represented as an allyl ester of dimer acid with the following structure.

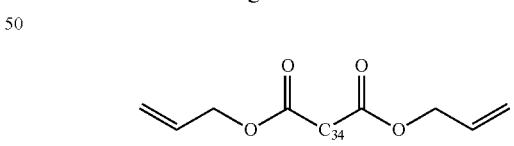

Additionally, linear allyl esters having the carbon content of the above allyl esters of a neoacid may also be used in the process described herein. One example of such a compound is an allyl ester of decanoate acid:

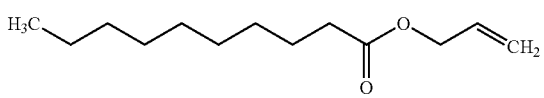

An example list of suitable vinyl esters includes the following esters:

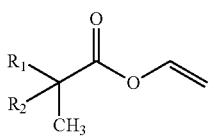

$R_1 + R_2$ contain combined 7 carbons
VeoVa 10™

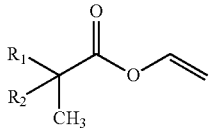

$R_1 + R_2$ contain combined 6 carbons
VeoVa 9™

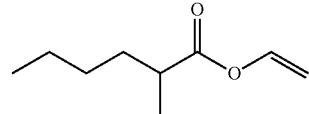

vinyl 2-ethylhexanoate

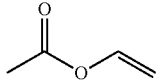

vinyl acetate

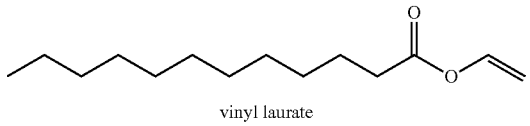

vinyl laurate

In one embodiment, a vinyl carboxylate or allyl carboxylate (a vinyl ester or allyl ester of a carboxylic acid) having 9 or more carbon atoms, such as from 9 to 30 carbon atoms, from the backbone and any attached functional groups may be used to form the epoxyethyl carboxylate or glycidal carboxylate compounds. Thus, one embodiment of the starting material may be represented by the following formulae:

$R_1COOCH=CH_2$ (vinyl carboxylate)

$R_1'COOCH_2CH=CH_2$ (allyl carboxylate)

with $R_1$ is a mono or polyvalent radical of 6 or more carbon atoms, such as from 6 to 100, for example, from 6 to 30 carbon atoms, wherein $R_1$ optionally contains 1 or more heteroatoms, wherein n corresponds to the number of ester groups. $R_1'$ is a mono or polyvalent radical of 5 or more carbon atoms, such as from 5 to 100, for example from 5 to 30 carbon atoms, wherein $R_1'$ optionally contains 1 or more heteroatoms, wherein n corresponds to the number of ester groups, and wherein n is an integer of 1 or greater, such as ranging from 1 to 6. Additionally, $R_1$ and $R_1'$ may comprise a secondary alkyl group of from 6 to 100 carbon atoms, such as from 6 to 30 carbon atoms, wherein R or R' optionally contains 1 or more heteroatoms, and/or a tertiary alkyl group of from 6 to 100 carbon atoms, such as from 6 to 30 carbon atoms, wherein R or R' optionally contains 1 or more heteroatoms.

Examples of such vinyl carboxylate or allyl carboxylate starting compounds include an allyl ester of a dimer acid, allyl ester of versatic-10 acid, diallyl ester of tetrahydrophthalic acid, diallyl ester of terephthalic acid, diallyl ester of succinic acid, allyl ester of salicylic acid, diallyl ester of phthalic acid, diallyl ester of methyl hexahydrophthalic acid, diallyl ester of oxalic acid, diallyl ester of hexahydrophobic acid, allyl ester of benzoic acid, allyl ester of 3 phenyl propionic acid, and tetra allyl ester of 1,2,3,4 tetracarboxybutane, allyl ester of neodecanoic acid, allyl ester of cyclohexane-1,2,4-tricarboxylic acid (H-TMA), respective vinyl-containing combinations thereof, respective allyl-containing combinations thereof, and combinations thereof.

Examples of epoxyethyl carboxylate or glycidal carboxylate product compounds made from the processes described herein include a diglycidyl ester of dimer acid, glycidyl ester of versatic 10 fatty acid, diglycidyl ester of tetrahydrophthalic acid, diglycidyl ester of terephthalic acid, diglycidyl ester of succinic acid, diglycidyl ester of salicylic acid, diglycidyl ester of phthalic acid, diglycidyl ester of methyl-hexahydrophthalic acid, diglycidyl ester of oxalic acid, diglycidyl ester of hexahydrophthalic acid, diglycidyl ester of benzoic acid, diglycidyl ester of 3-phenylpropionic acid, tetraglycidyl ester of tetracarboxybutane, triglycidyl ester of cyclohexane-1,2, 4-tricarboxylic acid (H-TMA), and combinations thereof.

As shown above, olefinically unsaturated carboxylic acids may also be used as starting material for the allyl or vinyl ester, such as (meth)acrylic acid. Such olefinically unsaturated carboxylic acids may also be aromatic carboxylic acids, and the aromatic unsaturated bonds are not epoxidized in the current process. The starting material may be is represented by the formulae:

$R'COOCH=CH_2$ (vinyl carboxylate)

$R'COOCH_2CH=CH_2$ (allyl carboxylate)

wherein R' represents an alkyl group of from 1 to 30 carbon atoms, such as a secondary alkyl group of from 3 to 30 carbon atoms or a tertiary alkyl group of from 4 to 30 carbon atoms. Alternatively, R' represents an alkyl group of from 1 to 29 carbon atoms, such as a secondary alkyl group of from 3 to 29 carbon atoms or a tertiary alkyl group of from 4 to 29 carbon atoms. In a further alternative embodiment, the starting material comprises R' of an alkyl group of from 5 to 29 carbon atoms, such as a secondary alkyl group of from 5 to 29 carbon atoms or a tertiary alkyl group of from 5 to 29 carbon atoms Suitable examples include vinyl acetate, allyl acetate, vinyl 2-butanoate, allyl 2-butanoate, vinyl pivalate, allyl pivalate, vinyl neononanoate, allyl neononanoate, vinyl neodecanoate, allyl neodecanoate (wherein "neo" refers to highly branched acids), and combinations thereof.

The epoxidation products of the vinyl esters of highly branched acids are believed to be novel. Accordingly, this invention also relates to epoxyethyl esters of neoacids (wherein R is a tertiary alkyl group) having from 5 to 30 (or 5 to 29) carbon atoms in the acid moiety.

The catalytic oxidation of the present invention may be carried out preferably using hydrogen peroxide as oxidant. Other oxidants may be used, i.e. as precursor to the hydrogen peroxide, but given the availability and to reduce environmental impact hydrogen peroxide is the preferred oxidant. Hydrogen peroxide has strong oxidizing properties. The peroxide may be used in an aqueous solution. The concentration of hydrogen peroxide may vary, from 15% to 98% (propellant grade), with a preference for industrial grades varying from 20 to 80%, such as from 30 to 70%. Other oxidants that may be used include organic peroxides, peracids, and combinations thereof.

To ensure optimal oxidant efficiency, the oxidant may be added to the aqueous reaction medium at a rate about equal to the reaction rate of the catalytic oxidation. The catalytic oxidation may be performed in a batch process, in a continuous process or in a semi-continuous process. Indeed, the process may be modified in various aspects without departing from the gist of the invention.

By way of general example the catalytic oxidation of VeoVa™ 10 ester (the vinyl ester of a highly branched acid, having 10 carbon atoms in the acid moiety) and allyl 1,2-ethylbutanoate and allyl methacrylate are is described hereafter.

The catalytic oxidation may be performed in a common stirred tank reactor provided with a means of stirring. The catalyst, aqueous reaction medium and reactants may be added in batch, or the reactants may be added over a period of time. If hydrogen peroxide is added during the reaction, then it is added to either the (stirred) organic phase comprising the ester, if any, or the (stirred) aqueous reaction medium. In (semi)continuous operations, various recycling streams may be used to control the reaction conditions, for example, maintained at a temperature of between 5° C. and 40° C., and to optimize the production rate.

The following examples will more fully illustrate selected embodiments of this invention. All parts, percentages and proportions referred to herein and in the appended claims are by weight unless otherwise indicated.

EXPERIMENTAL

The catalytic oxidation was carried out with a binuclear manganese complex as catalyst of the formula:

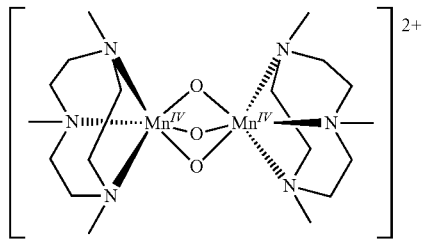

with $(CH_3COO^-)_2$ as the non-coordinating counter ion.

In the examples according to the invention an oxalate/oxalic acid buffer was used, with 35% aqueous $H_2O_2$ as oxidant, and water (pure) as aqueous reaction medium. The experiments were carried out with VeoVa™ 10 ester as a starting material or with the corresponding allyl esters (which is made in line with the procedure set out in WO03024914) allyl methacrylate and allyl 2-ethylbutanoate.

Example 1

A comparative was run using the system described by De Vos et al. (Epoxidation of Terminal or Electron-deficient Olefins with $H_2O_2$, catalysed by Mn-trimethyltriazacyclonane Complexes in the presence of Oxalate Buffer", Tetrahedron Letters 39 (1998) 3221-3224) for epoxidation of allyl acetate with hydrogen peroxide as the oxidant, with the exception that a maximum of 10% co-solvent (acetonitrile) in water was used. All the other concentrations were the same as described by the De Vos et al.

A solution of manganese sulphate monohydrate in water (0.1 mmol in 10 ml) and tmtacn in acetonitrile (0.15 mmol in 10 ml) were mixed and diluted with water (60 ml). An oxalic acid/oxalate buffer solution (0.15 mmol oxalic acid/0.15 mmol oxalate in 10 ml water) was added and finally allyl acetate (6.7 g, 67 mmol) was added to the reaction mixture, which is maintained at 5° C. An excess of hydrogen peroxide is dosed (10 ml of a 35% aqueous solution) in 5 minutes and the reaction is stirred at 800 rpm for 2 hours. The turnover number towards the epoxide is 460 after 2 hours. The yield of the epoxide based on the minor component (allyl acetate) is 47.6 mmol. The selectivity towards glycidyl ester is 95 mol % on total converted allyl ester. Prior art claimed 99% epoxide yield in 0.3 h time period with 70% acetonitrile as solvent. As shown in example 1, water as a solvent decreased the catalyst activity of the system.

Example 2

In the examples according to the invention a binuclear manganese complex (as shown in the beginning of the Experimental section) in an amount of 0.023 mmol was used in combination with an oxalate/oxalic acid buffer (4.14 mmol) in pure water (100 ml) as aqueous reaction medium. Oxidant used was 35% aqueous $H_2O_2$. The pH of the aqueous phase was stabilized at 3.6 by adding oxalic acid with a titrator and the temperature was maintained trough out the experiment at 5° C. The reaction was performed in a four necked glass reactor facilitated with a mechanical stirrer, cooling jacket and a bottom valve.

The experiments were carried out with the allyl esters allyl methacrylate and allyl 2-ethylbutanoate (which is made in line with the procedure set out in WO03024914) or the vinyl ester VeoVa™ 10 as starting material. The reaction was initiated with the addition of dilute $H_2O_2$ as oxidant. Dosing rate is 5 mL/h for 2 hours into the reaction mixture and stirring rate is 800 rpm. The unreacted hydrogen peroxide in the reactor was killed with $Na_2SO_3$ (saturated solution). Then the organic phase was analyzed for epoxide (desired product) and diol content (byproduct) by Epoxy Group Content determination (titration) and gas chromatography.

Example 2A

The catalytic epoxidation of 40 grams of allyl methacrylate was carried out as described above. Conversion towards glycidyl ester is 64 mmol after 2 hours. Selectivity towards glycidyl ester is 88 mol % (of which 58% selectivity for mono-epoxide glycidyl ether) on total converted allyl ester. Turnover number towards epoxide is 2800.

Example 2B

The catalytic epoxidation of 40 grams of allyl 2-ethylbutanoate was carried out similar to example 1. Conversion towards glycidyl ester is 50 mmol. Selectivity towards glycidyl ester is 83 mol % on total converted allyl ester. Turnover number towards epoxide is 2200.

Example 2C

The catalytic epoxidation of 100 grams of VeoVa™ 10 was carried out similar to example 1. Triton X-100 was added in the aqueous phase with a concentration of 0.5 wt %. Yield of epoxide based on the minor component ($H_2O_2$) is 5.3 mmol Selectivity towards glycidyl ester is 58 mol % on total converted allyl ester. Turnover number towards epoxide is 230.

Example 3

The catalytic epoxidation of VeoVa™ 10 ester was carried out with $[(TmTacn)_2 Mn^{IV}_2(\mu-O)_3]^{2+}(CH_3COO)_2$ as catalyst at 5° C. in a four necked glass reactor facilitated with a mechanical stirrer, cooling jacket and a bottom valve. The ratio of catalyst: co-catalysts was 1:60. About 23 µmol of catalyst was added in 100 mL of water followed by the addition of 0.675 mmol of sodium oxalate and 0.675 mmol of oxalic acid into the glass reactor under stirring conditions. Triton X 100 was added in the aqueous phase with a concentration of 1% by weight. The reaction was initiated with the addition of dilute $H_2O_2$ as oxidant. Dosing rate is 10 mL/h into the reaction solution. Dosing of oxidant was completed in first 80 min. After the reaction the aqueous solution in the reactor was analyzed to determine the residual level of $H_2O_2$. The unreacted hydrogen peroxide in the reactor was killed with $Na_2SO_3$. Then the organic phase was analyzed for epoxide content.

Example 4

The catalytic epoxidation of allyl methacrylate may be carried out similar to example 1 above, however with $[(TMTACN)_2 \, Mn^{IV}_2(\mu-O)_3]^{2+}(PF_6)_2$ in the presence of oxalate as buffer. After reaction the aqueous solution in the reactor may be analyzed to determine the residual level of $H_2O_2$. The unreacted hydrogen peroxide in the reactor may be killed with $Na_2SO_3$. Then the organic phase may be analyzed for epoxide content by titration with perchloric acid at 20° C., GC-MS analysis can also be used in order to measure selectivity to the desired product.

What is claimed is:

1. A process for the epoxidation of a vinyl carboxylate or an allyl carboxylate, comprising:
   reacting a vinyl carboxylate or an allyl carboxylate using an oxidant and a water-soluble manganese complex in an aqueous reaction medium, wherein the aqueous reaction medium comprises a 100% water phase excluding any of the vinyl carboxylate or the allyl carboxylate and/or the corresponding oxides dissolved therein, wherein the molar ratio of a vinyl carboxylate or an allyl carboxylate to oxidant is from greater than 1:1 to 12:1 and wherein the water-soluble manganese complex comprises:
   a mononuclear species of the general formula (I):

[LMnX₃]Y  (I), or a binuclear species of the general formula (II):

[LMn(µ-X)₃MnL]Y$_n$  (II), wherein Mn is a manganese; each L is independently a polydentate ligand of triazacyclononane or a substituted triazacyclononane, each X is independently a coordinating species selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, and R is a $C_1$-$C_{20}$ radical selected from the group consisting of alkyl, cycloalkyl, aryl, benzyl and combinations thereof, and each µ-X is independently a bridging coordinating species selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, and R is a $C_1$-$C_{10}$ radical selected from the group consisting of alkyl, cycloalkyl, aryl, benzyl and combinations thereof,
   wherein Y is a non-coordinating counter ion selected from the group consisting of $RO^-$, $Cl^-$, $Br^-$, $I^-$, $F^-$, $SO_4^{2-}$, $RCOO^-$, $PF_6^-$, acetate, tosylate, triflate, and a combination thereof, and R is a $C_1$-$C_{20}$ radical selected from the group consisting of alkyl, cycloalkyl, aryl, benzyl and combinations thereof, n is 1 or 2, and wherein the aqueous reaction medium further comprises a buffer system to stabilize the pH and the epoxidation is carried out at a pH in the range of from 2 to 5, and
   wherein the vinyl carboxylate or the allyl carboxylate is represented by an ester of the following formulae:

$R_1(C(O)OCH=CH_2)_n$; or

$R_1'(C(O)OCH_2CH=CH_2)_n$, wherein $R_1$ is a mono or polyvalent radical of 6 or more carbon atoms and $R_1'$ is a mono or polyvalent radical of 5 or more carbon atoms, wherein n corresponds to the number of ester groups and comprises an integer of 1 or greater, and wherein the total number of carbon atoms in the ester comprises 9 or more carbon atoms, wherein $R_1$ optionally contains 1 or more heteroatoms, and wherein $R_1'$ optionally contains 1 or more heteroatoms.

2. The process of claim 1, wherein the reaction further comprises stirring.

3. The process of claim 1, wherein a binuclear water-soluble manganese complex comprises a catalyst.

4. The process of claim 1, wherein the catalyst comprises a molar ratio of catalyst versus the oxidant of from 1:100 to 1:10,000,000.

5. The process of claim 1, wherein the aqueous reaction medium is in a biphasic system comprising an organic phase and the aqueous reaction medium.

6. The process of claim 1, wherein the oxidant comprises hydrogen peroxide, dilute hydrogen peroxide, or precursors of hydrogen peroxide.

7. The process of claim 1, wherein the molar ratio of the vinyl carboxylate or allyl carboxylate to the oxidant is from 2:1 to 10:1.

8. The process of claim 1 wherein the allyl carboxylate is selected from non-aromatic cyclic compounds, aliphatic functionalized allyl esters of nine or more carbon atoms, aromatic mono or di allyl esters of 15 carbon atoms or more, aromatic functionalized mono, bis tris or poly allyl esters of 11 or more carbon atoms, non-aromatic cyclical mono or di allyl esters, tri allyl esters, and combinations thereof.

9. The process of claim 1 wherein the vinyl carboxylate or the allyl carboxylate is selected from the group consisting of vinyl neononanoate, allyl neononanonate, vinyl neodecanoate, allyl neodecanoate, and combinations thereof.

10. The process of claim 1, wherein the oxidant is added to the aqueous reaction medium at a rate about equal to the reaction rate.

11. The process of claim 1, wherein the reacting is performed in a batch process, in a continuous process or in a semi-continuous process.

12. The process of claim 1, wherein the vinyl carboxylate or the allyl carboxylate is represented by an ester of the following formulae:

$R_1(C(O)OCH=CH_2)_n$; or

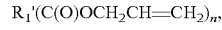

$R_1'(C(O)OCH_2CH=CH_2)_n$, wherein $R_1$ is a mono or polyvalent radical from 6 to 100 carbon atoms and $R_1'$ is a mono or polyvalent radical from 5 to 100 carbon atoms, wherein n corresponds to the number of ester groups and comprises an integer of 1 or greater, and wherein the total number of carbon atoms in the ester comprises 9 or more carbon atoms.

13. The process of claim 1, wherein the aqueous reaction medium comprises a buffer system to catalyst molar ratio of 60:1 to 300:1.

14. The process of claim 1, wherein the manganese complex comprises the formula $[Mn^{IV}_2(\mu\text{-}O)_3L_2]Y_2$, wherein L is a triazacyclononane or substituted triazacyclononane and the counterion Y is $PF_6^-$ or $CH_3CO_2^-$.

15. The process of claim 1, wherein the vinyl carboxylate or the allyl carboxylate is represented by an ester of the following formulae:

$$R_1(C(O)OCH\!=\!CH_2)_n;\ or$$

$$R_1'(C(O)OCH_2CH\!=\!CH_2)_n,$$

wherein $R_1$ is a mono or polyvalent radical of 6 or more carbon atoms and $R_1'$ is a mono or polyvalent radical of 5 or more carbon atoms, wherein n corresponds to the number of ester groups and comprises an integer of 1 or greater, and wherein the total number of carbon atoms in the ester comprises 9 or more carbon atoms, wherein $R_1$ optionally contains 1 or more heteroatoms, and wherein $R_1'$ optionally contains 1 or more heteroatoms.

16. The process of claim 12, wherein the vinyl carboxylate or the allyl carboxylate is selected from the group of allyl ester of a dimer acid, allyl ester of versatic-10 acid, diallyl ester of tetrahydrophthalic acid, diallyl ester of terephthalic acid, diallyl ester of succinic acid, allyl ester of salicylic acid, diallyl ester of phthalic acid, diallyl ester of methyl hexahydrophthalic acid, diallyl ester of oxalic acid, diallyl ester of hexahydrophobic acid, allyl ester of benzoic acid, allyl ester of 3 phenyl propionic acid, and tetra allyl ester of 1,2,3,4 tetracarboxybutane, allyl ester of neodecanoic acid, allyl ester of cyclohexane-1,2,4-tricarboxylic acid (H-TMA), respective vinyl-containing combinations thereof, respective allyl-containing combinations thereof, and combinations thereof.

* * * * *